United States Patent [19]

Geluk

[11] Patent Number: 4,665,539
[45] Date of Patent: May 12, 1987

[54] METHOD AND APPARATUS FOR FORMING TOMOGRAPHIC IMAGES

[75] Inventor: Ronald J. Geluk, Nootdorp, Netherlands

[73] Assignee: N.V. Optische Industrie "de Oude Delft", Netherlands

[21] Appl. No.: 766,780

[22] Filed: Aug. 16, 1985

Related U.S. Application Data

[63] Continuation of Ser. No. 386,710, Jun. 9, 1982.

[30] Foreign Application Priority Data

Jun. 15, 1981 [NL] Netherlands .......................... 8102872

[51] Int. Cl.⁴ ...................... A61B 06/00; H05G 01/60
[52] U.S. Cl. ...................... 378/010; 364/414; 378/012; 378/026; 378/901
[58] Field of Search .............. 378/021, 022, 025, 026, 378/023, 024, 027, 009, 010, 011, 012, 014, 041, 042, 901, 002; 364/414

[56] References Cited

U.S. PATENT DOCUMENTS

| | | | |
|---|---|---|---|
| 4,002,917 | 1/1977 | Mayo | 378/014 |
| 4,031,395 | 6/1977 | Lemay | 378/010 |
| 4,064,440 | 12/1977 | Roder | 378/010 |
| 4,149,082 | 4/1979 | Haendle et al. | 378/041 |
| 4,160,167 | 7/1979 | Weiss et al. | 378/019 |
| 4,236,080 | 11/1980 | Heinzerling | 378/901 |

*Primary Examiner*—Craig E. Church
*Assistant Examiner*—T. N. Grigsby
*Attorney, Agent, or Firm*—Louis E. Marn

[57] ABSTRACT

A method of forming tomographic images in cross-sectional tomography, in which a body is irradiated by a flat X-ray beam at different angles for successively forming a plurality of profiles on an X-ray screen or an X-ray detector, and a tomogram is constructed from the profiles, wherein the body and the X-ray detector are kept stationary and that, for forming the different profiles, the source of the flat X-ray beam is moved in a relatively short path extending on the side of the body remote from the X-ray detector.

20 Claims, 3 Drawing Figures

METHOD AND APPARATUS FOR FORMING TOMOGRAPHIC IMAGES

This is a continuation of application Ser. No. 386,710, filed June 9, 1982.

The invention relates to a method and apparatus for forming tomographic images in cross-sectional tomography, in which a body is irradiated by a flat X-ray beam at different angles for forming a plurality of profiles on an X-ray detector, and a tomogram is constructed from these profiles.

In the present field a profile is a one-dimensional representation of the absorption characteristics of the body in a sectional plane coplanar with the flat X-ray beam. A tomogram is an image of a cross-section of the body, which cross-section is coplanar with the flat X-ray beam ("cross-sectional" tomography).

Such a method is known from e.g. Dutch patent application No. 76,05254. Furthermore, such a method is disclosed in the article "Three-dimensional Reconstruction from Radiographs and Electron Micrographs" by G. N. Ramachandran and A. V. Lakshminarayanan in Proceedings of the National Academy of Sciences U.S.A., Vol. 68, No. 9, pages 2236–2440, September 1971.

Moreover, such a method is embodied in the "X-ray body scanner" of General Electric Company described in "Electronics", Dec. 25, 1975, pages 33–34.

In all of these prior art techniques, the body of which a cross-sectional image is to be formed is rotated relative to the source of the X-ray beam about an axis normal to the sectional plane. It is also possible to have the X-ray source orbit around the stationary body, as this is done in the apparatus described in "Electronics".

A drawback inherent in the prior art techniques is that rather bulky equipment including rotating components is required. Besides, problems of a mechanical nature, this entails the additional drawback that the forming of a tomogram takes a relatively long period of time unless the number of X-raying circuits is multiplied.

It is an object of the invention to simplify the prior art techniques.

To achieve this object, in accordance with the invention a method of the above type is characterized in that the body and the X-ray screen are kept stationary and that, for forming the different profiles, the source of the flat X-ray beam is moved in a relatively short path extending on the side of the body remote from the X-ray detector.

Furthermore, in accordance with the invention an apparatus for applying this method is characterized by the presence of control means comprising a device adapted to move the X-ray source, when operative, in a relatively short path extending on the side of the body remote from the X-ray detector.

The invention will be described in greater detail hereinafter with reference to the accompanying drawings, in which:

FIG. 1 schematically shows the manner of producing profiles in accordance with the invention;

Figure 1:
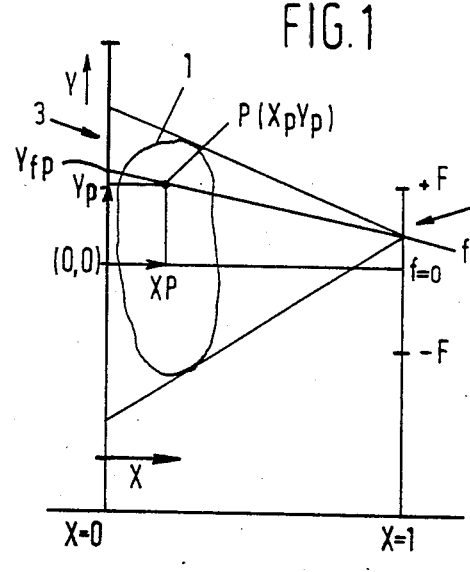

FIG. 1 schematically shows the manner of producing profiles in accordance with the invention. Reference numeral 1 denotes a body extending normal to the plane of the drawing, of which body a cross-sectional image or tomogram corresponding with the section situated in the plane of the drawing has to be formed. The body 1 may be the body of a patient to be examined as well as a random object. X-ray source 2 to be described hereinafter is shown on the right-hand side of the body 1 and a conventional X-ray detector 3 for X-radiation is shown on the left-hand side of the body, which X-ray detector receives the X-radiation transmitted by the body and converts it into, for example, a light image.

If a flat X-ray beam is used in known per se manner for forming a tomogram, the X-ray detector may have a one-dimensional configuration.

In accordance with the invention, the X-ray detector and the body to be irradiated may be stationary mounted, provided the X-ray source can move relative to the body 1, for example in a path between $-F$ and $+F$, as shown in FIG. 1. The movement of the X-ray source is preferably performed in a direction parallel to the substantially one-dimensional detector 3.

An X-ray tube moving between $-F$ and $+F$ may be used for the purpose. In a preferred embodiment, however, the X-ray source is an X-ray tube having a line- or strip-shaped anode extending at least from $-F$ to $+F$, which anode is struck point by point in continuous or step-wise fashion by an electron beam produced by an electron source and suitably deflected. Each point of the anode struck by the electron beam will constitute the X-ray focus from which the body 1 is irradiated. An example of such an X-ray tube is disclosed in German Offenlegungsschrift No. 2,538,517.

Should the anode of the X-ray tube be too short, two or more tubes may be used which are mounted so that their anodes are in line. The deflections of the respective electron beams should then be adjusted to each other.

The invention is based on the concept that, when moving the X-ray focus between $-F$ and $+F$ through a sufficient number of intermediate positions, the information obtained is sufficient for forming an adequate tomogram, whereas in the prior art techniques a rotation of the X-ray source relative to the body through at least 180° is required for producing the profiles. To distinguish the present technique from the prior art techniques, the former may be designated by the term translation tomography or, more specifically, focus translation tomography.

As an electron beam can be moved over the anode from $-F$ to $+F$ at a very high speed, the period of time required for obtaining the information necessary for forming a tomogram is accordingly very brief, so that the manner in which the profiles are formed no longer forms a impediment to achieving dynamic sectional images of, for example, the beating heart.

In each position of the X-ray focus a unique profile is formed on the X-ray detector. As, theoretically speaking, the X-ray focus can take an unlimited number of different positions between $-F$ and $+F$, an unlimited number of associated unique profiles can be formed. These profiles contain sufficient information for forming a tomographic image. In actual practice, just as this is done in the conventional techniques, self-evidently a limited number of profiles sufficient for forming a tomogram of the quality desired is used.

Using a standard television rhythm in scanning the profile information presented on the detector 3, the position f of the X-ray focus should move from $-F$ to $+F$ within 18 msec with a retrace period of $<2$ msec.

This movement may be a continuous or a step-wise one. In that case, the detector is scanned at the television line rate of 15,625 Hz, so that 312 different profiles are converted into a television signal during a period of focus movement. Due to the system of interlaced scanning customary in television systems, during the subsequent period of focus movement 313 different profiles associated with intermediate focus positions are converted into a television signal. Thus every 40 msec 625 different profiles are converted into a television signal. A tomogram can be formed in different manners from the information present in these television signals. For example, this information may be applied to a computer calculating therefrom the brightness of each image element of the tomogram to be constructed. At the present computer rates, no instantaneous construction of the tomogram is possible.

In accordance with a further elaboration of the idea underlying the present invention, the following method of constructing the tomogram is used.

The profiles associated with one and the same section of the body 1 are recorded in juxtaposition with interspaces proportional to the interspaces between the respective focus positions f. This collection of parallel profiles will be called a "profilegram" hereinafter.

Figure 2:
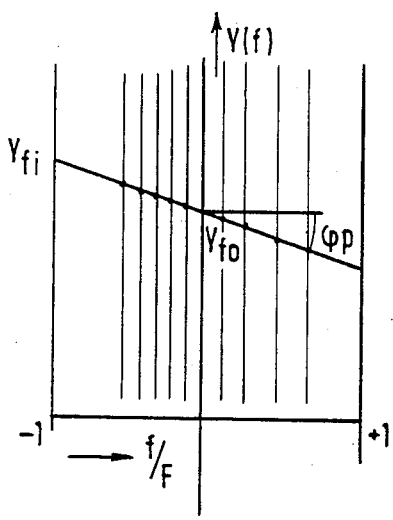
FIG. 2 illustrates a so-called "profilegram"

Such a profilegram is shown in FIG. 2. Defining F as the maximum distance between the X-ray focus and a selected zero point f=0 (see FIG. 1), when the X-ray focus is in point −F there applies f/F=−1. Consequently, the associated profile is situated on the extreme left in the profilegram of FIG. 2. Similarly, the profile associated with f=0 is situated in the center of the profilegram and the profile associated with f=+F is situated on the extreme right in the profilegram.

In FIG. 1 an x-y system of coordinates is drawn so that the X-ray detector 3 is situated on the line x=0, i.e. the y-axis, and the path of the X-ray focus is on the line x=1. Consequently, each point P of the section of body 1 in the x-y plane has the coordinates P $(x_p, y_p)$.

Considering point P $(x_p, y_p)$ of the body 1 shown in FIG. 1, the shadow of this point on the detector (i.e. in the plane x=0) has a position $Y_{fp}$ depending on the instantaneous position f of the X-ray focus and on both $x_p$ and $y_p$.

It can be calculated that:

$$y_{fp} = y_p \left( \frac{1}{1 - x_p} \right) - f x_p \left( \frac{1}{1 - x_p} \right).$$

In the profilegram each point P $(x_p, y_p)$ describes a straight line through the point $y_{f0}$ at an angle $\phi_p$. The point $y_{f0}$ is the shadow of P $(x_p, y_p)$ corresponding with the focus position f=0. Consequently, $yf0 = y_p/1 - x_p$. The angle $\phi_p$ is defined by $$\text{tg}\phi_p = \frac{x_p}{1 - x_p},$$

which means that the angle $\phi_p$ corresponds directly with $x_p$.

Consequently, each point of the irradiated section of the body 1 corresponds with an associated straight line in the profilegram and, conversely, each straight line in the profilegram corresponds with a certain point of the x-y plane of FIG. 1.

The density of a point $(x_p, y_p)$ therefore corresponds with the intensity integrated along the associated line in the profilegram.

The above shows that, in its simplest form, a tomogram can be constructed from the profilegram by successively taking each point on the line f/F=0 or a line parallel thereto in the profilegram and then successively integrating the brightness along all of the lines passing through the point in question. Other linear combinations of intensities of points in the profilegram are possible too. In combination therewith, if desired other techniques for improving the image quality may be used, which techniques need not be of a linear nature.

Figure 3:
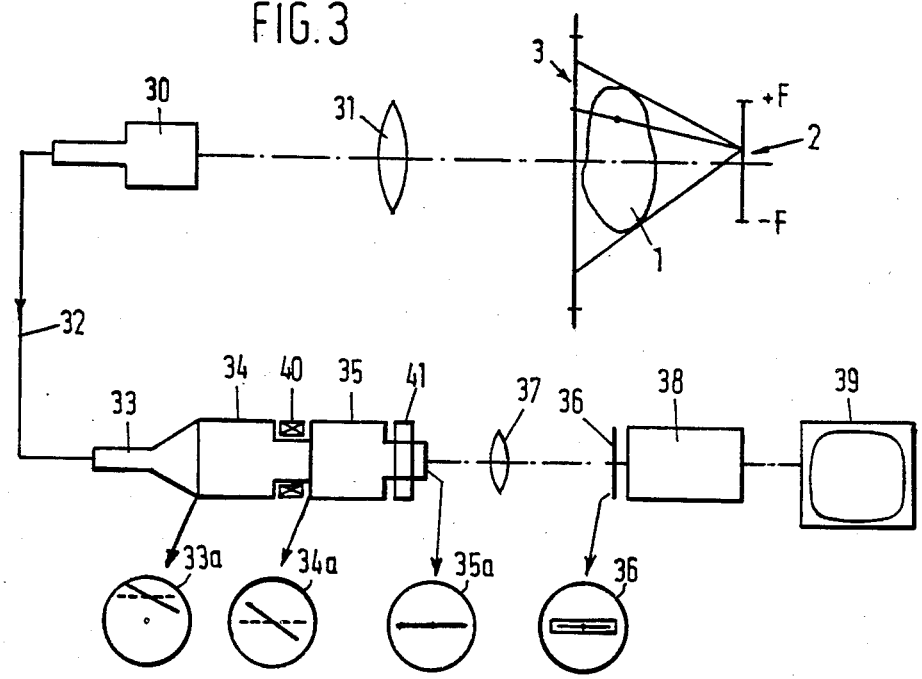
FIG. 3 shows an example of an apparatus for applying the method according to the invention.

The construction method described above can be realized by the device schematically shown in FIG. 3.

The X-ray detector 3 on which the profiles are successively formed is viewed, if desired through the intermediary of an optical system 31, by a television camera 30 the vertical deflection of which has been deactivated. The profiles received by the television camera 30 are applied in customary manner in the form of an electrical signal to the signal input of a cathode ray tube 33 via a line 32. The cathode ray tube has a phosphorescent screen 33a of medium long persistence and is controlled so that the profiles are reproduced in juxtaposition on this screen 33a. As a result, the profiles are simultaneously visible on the screen for a period of time, so that the image on the screen corresponds with the complete profilegram for this period of time. This image is electro-optically reproduced by means of a first image intensifier 34 including deflection means 40 controlled so that each point on the line f/F=0 of the profilegram successively coincides with a suitably selected reference point on the anode screen 34a of the image intensifier 34. Consequently, a translation is required for this purpose.

The output image of the image intensifier 34 is applied to a second image intensifier 35 including image rotating means 41 generating a varying axial magnetic field so that in each translated position a rotation of all of the lines passing through the reference point into a fixed position, for example the horizontal one, is successively realized. These horizontal lines on the anode screen 35a of the image intensifier 35 are subsequently detected via a slotted mask 36, which mask may be preceeded by an optical device 37, by a device, for example a photomultiplier tube 38, which device performs an integrating operation over the mask, so that each time the brightness integrated along a horizontal line will be available in the form of an electrical signal at the output of the photomultiplier tube. This electrical signal can be used for controlling the signal input of a television monitor 39. The deflection devices of this television monitor are controlled by signals corresponding with the translation performed by the image intensifier 34 and the rotation performed by the image intensifier 35 respectively. The television monitor thus displays an image (tomogram) of the cross-section of the body 1.

Various modifications of the method and apparatus described above are possible. For example, in FIGS. 1 and 3 the detector extends as a straight line but this line may just as well be slightly curved. The resultant distortion can be compensated for in manners obvious to the worker in the art, for example by means of the optical device 31.

Furthermore, as stated earlier, the X-ray focus can traverse the path from −F to +F in continuous as well as in step-wise fashion. In the latter mode of operation a proper distinction between the profiles associated with the different focus positions is quaranteed. If desired, the speed or the size of the steps may be varied along the path in accordance with a suitable function, for example a sinusoidal one.

The profiles may be directly written on the screen of a cathode ray tube in the form of a profilegram and further processed in the manner described above but the profiles may just as well be stored in a storage medium so as to be subjected to some sort of further processing at a later instant. In.both events it is necessary to indicate the focus position associated with each profile. In the arrangement shown in FIG. 3, this may be realized in a simple manner by having the horizontal deflection of the cathode ray tube take place in correspondence with the movement of the X-ray focus.

In principle, it is also possible to realize the translation as well as the rotation of the profilegram by means of a single image intensifier to be specially designed for this purpose, which intensifier is provided with suitable deflection and image-rotating means.

As stated above, a slotted mask is used in the apparatus according to the invention. As the slot not only comprises the line in the profilegram associated with the image element to be constructed at that instant but is at the same time crossed by lines of the profilegram associated with other image elements, a degree of unsharpness will occur in the final tomogram. This unsharpness may be regarded as being the result of a point-spread function to be determined by experimental and iterative methods. The effects of this point-spread function can be eliminated by using a different mask instead of or in combination with a slotted mask. This technique is known per se from Dutch patent application No. 76,05254. As the technique disclosed in this application No. 76,05254 will normally require a function, the so-called deconvolution function, to be incorporated in the mask to be used, which function includes positive as well as negative portions, in that case a single mask will not suffice and a first mask incorporating the positive portion of the deconvolution function and a second mask incorporating the negative portion of the deconvolution function will have to be used. In consequence, in the manner described in Dutch application No. 76,05254 a beam splitter is required as well as a second photomultiplier tube device, associated with the second mask. The output signals of the photomultiplier tubes are subtracted from each other prior to their application to the television monitor or, in general, image-forming device.

The above and similar modifications are considered to be obvious to the worker in the art and to fall with the scope of the invention.

I claim:

1. A novel method for forming tomographic images from information obtained from an X-ray detector, the steps comprising:
    (a) positioning a body in front of said X-ray detector;
    (b) irradiating said body by a flat X-ray beam provided by an X-ray source;
    (c) moving said X-ray source along a short path lying in the same plane as said flat X-ray beam during step (b) to successively form from different positions along said path a plurality of profiles on said X-ray detector;
    (d) maintaining said body and said X-ray detector stationary during steps (b) and (c); and
    (e) constructing cross-sectional transaxial tomographic images from said plurality of profiles by writing said profiles in juxtaposition into a storage medium for forming a profilegram and determining intensity of an image element of said cross-sectional transaxial tomographic image to be formed by combining intensities linearly by integrating intensity along a straight line in said profilegram intersecting said profiles.

2. The novel method for forming tomographic images as set forth in claim 1, characterized in that said short path of said flat X-ray beam is rectilinear.

3. The novel method for forming tomographic images as set forth in claim 2, characterized in that said rectilinear short path extends substantially parallel to said X-ray detector means.

4. The novel method for forming tomographic images as set forth in claims 1, 2 or 3, characterized in that said flat X-ray source is an X-ray tube having an anode to be struck by a swivelling electron beam, an instantaneous point where said electron beam strikes said anode constituting an instantaneous source of said flat X-ray beam and said anode comprising said relatively short path.

5. The novel method for forming tomographic images as set forth in claims 1 or 3, characterized in that said flat X-ray beam traverses said relatively short path in step-wise fashion.

6. The novel method for forming tomographic images as set forth in claim 1, characterized in that determination of intensity of said image elements of said cross-sectional transaxial tomographic images to be formed is such that said profilegram is detected through at least one mask by a device performing an integrating operation over said at least one mask, said profilegram and said at least one mask being subjected to a translation and, in each translated position, a rotation relative to each other.

7. The novel method for forming tomographic images as set forth in claim 6, characterized in that said at least one mask is a slotted mask.

8. The novel method for forming tomographic images as set forth in claims 6 or 7, characterized in that an output signal of said device performing an integrating operation over said at least one mask is used for controlling an image reproducing device.

9. A novel apparatus for forming tomographic images, which comprises:
    an X-ray detector means;
    means for positioning a body in front of said X-ray detector means;
    means for generating a flat X-ray beam;
    means for moving said means for generating a flat X-ray beam in a short path during generation of said flat X-ray beam to successively form from different positions along said path a plurality of profiles on said X-ray detector means, said X-ray detector means and said body being maintained stationary during movement of said means for generating a flat X-ray beam;
    means for constructing cross-sectional transaxial tomographic images from said plurality of profiles by writing said profiles in juxtaposition into a storage medium for forming a profilegram and determining intensity of an image element of said cross-sectional transaxial tomographic image to be formed by combining intensities of points of said profilegram;

a television camera for picking up said successively formed profiles and converting said profiles into electrical signals; and a cathode ray tube having a memory screen or a screen of sufficiently long persistence and including a signal input for applying said electrical signals, a deflection means of said cathode ray tube being controlled to form a profilegram on said screen.

10. The novel apparatus for forming tomographic images as defined in claim 9, characterized in that said means for moving said means for generating said flat X-ray beam traverses said relatively short path in a step-wise fashion.

11. The novel apparatus for forming tomographic images as defined in claim 9, characterized in that said means for moving said means for generating a flat X-ray beam in said relatively short path courses a rectilinear path.

12. The novel apparatus for forming tomographic images as defined in claim 11, characterized in that said relatively short path extends substantially parallel to said X-ray detector means.

13. The novel apparatus for forming tomographic images as defined in claim 9, characterized in that said means for generating said flat X-ray beam comprises at least one fixedly mounted X-ray tube having a line-shaped anode activated by an electron beam generated by an electron gun mounted in said X-ray source, and wherein said means for moving said means for generating said flat X-ray beam comprises deflection means for said electron beam whereby application of deflection voltages to said deflection means causes said electron beam to perform a swivelling movement over said anode.

14. The novel apparatus for forming tomographic images as defined in claim 13, characterized in that said anode is a straight strip.

15. The novel apparatus for forming tomographic images as defined in claim 14, characterized in that said anode extends parallel to the X-ray detector means.

16. The novel apparatus for forming tomographic images as defined in claim 9, characterized in that said screen is optically coupled to a cathode window of a first image intensifier tube, said first image intensifier tube including deflection means controlled to translate an image of the profilegram formed on an anode screen of said image intensifier tube.

17. The novel apparatus for forming tomographic images as defined in claim 16, and further including a second image intensifier tube having a cathode window optically coupled with said anode screen of said first image intensifier tube, said second image intensifier tube comprising image rotating means controlled to rotate and image of the profilegram formed on the anode screen of said second image intensifier tube through a predetermined angle in each translated position realized by said first image intensifier tube.

18. The novel apparatus for forming tomographic images as defined in claim 17, characterized by at least one light detector adapted to integrate via an associated mask brightness distribution of said image formed on said anode screen of said second image intensifier tube in each rotated position realized by said second image intensifier tube, and to convert integrated brightness distribution into a corresponding electrical output signal.

19. The novel apparatus for forming tomographic images as defined in claim 18, characterized in that said mask is a slotted mask.

20. The novel apparatus for forming tomographic images as defined in claims 18 or 24, characterized in that said at least one light detector is applied to signal input of a television monitor.

* * * * *